United States Patent [19]

Holtkamp

[11] Patent Number: Plant 5,605

[45] Date of Patent: Dec. 17, 1985

[54] AFRICAN VIOLET PLANT NAMED IMPROVED ALABAMA

[75] Inventor: Reinhold Holtkamp, Isselburg, Fed. Rep. of Germany

[73] Assignee: Gessellschaftsvertrag uber die Ergindergemeinschaft "OPTIMARA", Rees Haffen, Fed. Rep. of Germany

[21] Appl. No.: 568,445

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Improved Alabama characterized by its vigorous and compact growth habit, strong and upright flower stems each of which carries 7–9 or more relatively large white-purple variegated frilled flowers, and by its relatively dark leaves.

1 Drawing Figure

The present invention comprises a new and distinct cultivar of African violet plant, botanically known as *Saintpaulia ionantha,* and named Improved Alabama.

The new cultivar was referred to during the breeding and selection process by the designation F 38/6, and is a product of a planned breeding program. The basic objective of the breeding program was to create a new African violet cultivar improving certain characteristics of the cultivar Alabama, disclosed in my U.S. Plant Pat. No. 4,373.

The new cultivar was originated from a cross made in a controlled breeding program in Isselburg, West Germany. The female, or seed parent was a cultivar designated B 242/3 Violet single. The male, or pollen parent was a cultivar designated D 157/0 White blue semi-double frilled.

The new cultivar was originated from a cross made in a controlled breeding program in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Improved Alabama has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn., under greenhouse conditions which closely approximate those generally used in commercial practice.

The following traits have been repeatedly observed and are determined to be basic characteristics of Improved Alabama, which in combination distinguish this African violet as a new and distinct cultivar;

1. Vigorous but compact growth habit, with little stretching of the leaf petioles.

2. Variegated flowers with the principal background color being white, and the center of the flower petals, and in certain instances the edges, being an intensive violet blue.

3. The single flowers are frilled at the edges.

4. The stems are average in length, but very strong and upright, with each stem carrying 7–9 or more flowers. As a result, a fairly rigid and tight bouquet is formed.

5. Attractive dark green and shiny leaves.

The new cultivar is most similar to Alabama, referred to above. In comparison to Alabama, the purple color in the variegated flowers is a more intense violet blue, the leaves are a darker green, the growth habit is more compact and non-stretching, and the flower stems are stronger, thereby providing a tight bouquet above the leaves.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 2:00 on Nov. 30 in Nashville, Tenn.

Botanical classification: *Saintpaulia ionantha,* Ramat. cv. Improved Alabama.

Parentage:

*Male parent.*—D 157/0 White blue semi-double frilled.

*Female parent.*—B 242/3 Violet single.

Propagation: The new cultivar holds its distinguishing characteristics through successive propagations by leaf cuttings and by division of shoots.

Plant: From 6 cm. to 8 cm. tall when grown in pots, and approximately 25 cm. in diameter when fully grown.

*Leaves.*—General form: Oval shape. Diameter: 60–70 mm. Texture: Leather-like. Aspect: Velvety, slightly shiny; hairy. Veins: Well Pronounced, light green. Color (upperside): Yellow green 147A. Color (underside): Yellow green 148D. Petiole: Light green; hairy.

*Flowers.*—Buds: Ball shape, light, green, with purple pattern. Sepals: Green. Calyx: Funnel shape. Aspect: Spear shape; hairy. Peduncle: Light green strong upright; hairy.

*Individual flowers.*—Size: 45–55 mm. Color: Upperside: Main color is white with the center portions of the flower petal being violet blue, 89B. Underside: Color is white variegated with violet blue 89C. Borne: On strong upright flower stems; 6–9 single flowers are carried on short wire-like pedicels. Shape: Violet shape, frilled. Corolla: Compact and above the leaves. Flowering time: In 9–10 weeks after potting, a saleable plant with a full bouquet is formed.

*Reproductive organs.*—Anthers: 2 composed of 4 cells. Filaments: Bright green ovary. Styles: Light purple with glassy stigma. Pollen color: Yellow.

*Roots.*—White when young and active; brownish when older.

*Disease resistance.*—Good as experienced to date.

General observations: Improved Alabama has a vigorous, compact and non-stretching growth habit. The variegated flowers are mainly white, with intense blue purple being formed at the centers and along the edges of certain of the flowers. The flowers are carried on stems which are average in length but strong thereby providing a tight flower bouquet well above the attractive dark green leaves.

I claim:

1. A new and distinct cultivar of African violet plant named Improved Alabama, as illustrated and described, and particularly characterized by its vigorous and compact growth habit, strong and upright flower stems each of which carries 7–9 or more relatively large white-purple variegated frilled flowers, and by its relatively dark leaves.

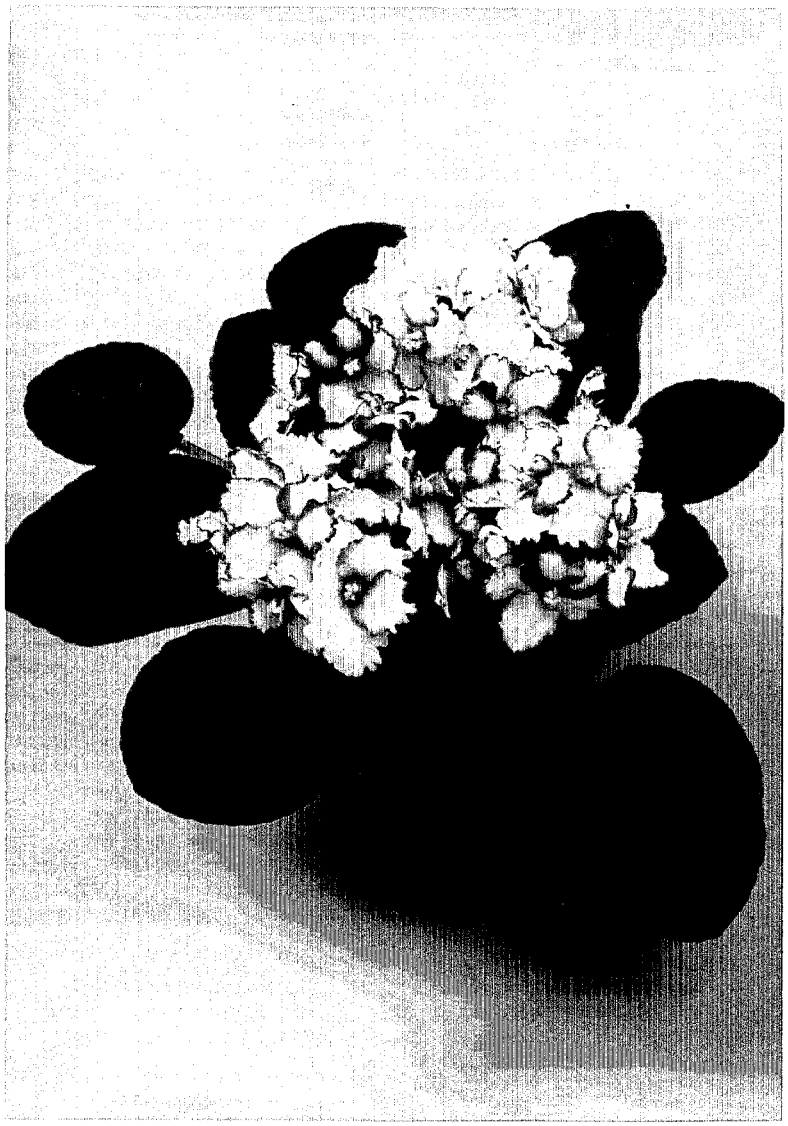

* * * * *